United States Patent [19]

Morii et al.

[11] Patent Number: 4,978,620

[45] Date of Patent: * Dec. 18, 1990

[54] PROCESS FOR SEPARATING SINGLE-CHAIN TPA AND DOUBLE-CHAIN FROM EACH OTHER

[75] Inventors: Mitsuyoshi Morii; Masaharu Ohoka, both of Yokohama; Toshihiko Suzuki, Tokyo; Katsuyuki Suzuki, Hiroshima; Nobuhiro Kawashima, Sagamihara; Noriko Morii; Kunizo Mori, both of Yokohama, all of Japan

[73] Assignee: Mitsui Toatsu Chemicals, Incorporated, Tokyo, Japan

[ * ] Notice: The portion of the term of this patent subsequent to Feb. 6, 2007 has been disclaimed.

[21] Appl. No.: 183,757

[22] PCT Filed: Aug. 10, 1987

[86] PCT No.: PCT/JP87/00598

§ 371 Date: Apr. 7, 1988

§ 102(e) Date: Apr. 7, 1988

[87] PCT Pub. No.: WO88/01294

PCT Pub. Date: Feb. 25, 1988

[30] Foreign Application Priority Data

Aug. 11, 1986 [JP] Japan .................................. 61-186850
May 14, 1987 [JP] Japan .................................. 62-115976

[51] Int. Cl.$^5$ ........................... C12N 9/64; C12N 9/48
[52] U.S. Cl. .................................... 435/226; 435/212; 435/219; 435/815
[58] Field of Search ............... 435/212, 215, 219, 226, 435/814, 815

[56] References Cited

FOREIGN PATENT DOCUMENTS 0112122 of 1984 European Pat. Off. .
8701389 3/1987 World Int. Prop. O. .......... 435/212

OTHER PUBLICATIONS

J. Biological Chemistry, vol. 257, pp. 2920 to 2925 in Mar. 25, 1982, by D. C. Rijken et al.
J. Biological Chemistry, vol. 256, pp. 7035 to 7041 in Jul. 10, 1981, by D. C. Rijken et al.
Methods in Enzymology, vol. 36, Part B, pp. 59 to 72 and 77 to 102, edited by W. B. Jakoky and Aleir Wilchele.

*Primary Examiner*—Elizabeth C. Weimar
*Assistant Examiner*—Charles L. Patterson, Jr.
*Attorney, Agent, or Firm*—Fisher, Christen & Sabol

[57] ABSTRACT

The distinction of tissue plasminogen activator, especially, the separation of its single-chain species and double-chain species is effected by using the Erythrina trypsin inhibitor which occurs in seeds of a plant of the Erythrina species.

1 Claim, No Drawings

PROCESS FOR SEPARATING SINGLE-CHAIN TPA AND DOUBLE-CHAIN FROM EACH OTHER

TECHNICAL FIELD

This invention relates to a novel process for selectively recovering single-chain tissue plasminogen activator (hereinafter called "tPA"), or single-chain tPA from an aqueous medium containing both single-chain tPA and double-chain tPA.

More specifically, it is concerned with a process for separating single-chain tPA and double-chain tPA from an aqueous medium, which contains both single-chain tPA and double-chain tPA, by using a carrier with the Erythrina trypsin inhibitor borne thereon.

Namely, this invention relates to a process for isolating and purifying single-chain tPA at a high purity from an aqueous medium containing both single-chain tPA and double-chain tPA and separating both tPAs from each other by using the Erythrina trypsin inhibitor (hereinafter abbreviated as "ETI") "which occurs in seeds of *Erythrina latissima* and other Erythrina plants and is an immobilized Kunitz inhibitor that serves as an inhibitor for trypsin, plasmin and tPA but does not act on urokinase" [F. J. Joubert et al., Hoppe Seyler's Z. Physiol. Chem. 362, 531–538 (1981)].

BACKGROUND ART

The following process has been known as one example of the use of ETI for the purification of tPA. Namely, the purification process comprises providing human melanoma cells, causing the cells to produce tPA in a serum-free medium, harvesting the culture crop, charging it into an ETI column to adsorb tPA, and then eluting ETI-adsorbed tPA with a 1–3M aqueous solution of potassium thiocyanate (Japanese Patent Laid-Open No. 118717/1984). This purification process is however a process for purifying tPA but does not relate to the separation and purification of single-chain tPA and double-chain tPA.

The present inventors have already developed inter alia a process for separating and removing tPA which occurs in a culture medium containing fetal calf serum, reacts to anti-human tPA antibody and has a molecular weight of 110,000±20,000 daltons as well as a process for culturing cells, in which tPA gene has been integrated by using recombinant DNA technology, and then separating tPA derived from host cells and tPA originated from human cells (Japanese Patent Laid-Open No. 168601/1985).

Substances having the above tPA activity include both single-chain and double-chain ones. It has been found that both of them have a molecular weight of about 70,000 daltons but the single-chain tPA and double-chain tPA are different in plasminogen activating ability and affinity to fibrins. Namely, it has been uncovered that double-chain tPA has plasminogen activating ability as high as about ten times compared with single-chain tPA (Japanese Patent Laid-Open No. 118717/1984) and on the other hand, single-chain tPA has greater affinity to fibrins compared with double-chain tPA and upon adsorption on fibrins, is converted very quickly into double-chain tPA. Single-chain tPA is therefore preferable for obtaining the desired activity to the maximum extent at the site of clots [D. C. Rijken, et al., J. Biol. Chem., 257, 2920–2925 (1982)].

As a method known for obtaining single-chain tPA, it has been known to add a proteolytic enzyme inhibitor upon culture of cells so as to inhibit the conversion from single-chain tPA into double-chain tPA (D. C. Rijken, et al., J. Biol. Chem., 256, 7035–7041 (1981)]. This method is however very difficult to suppress the conversion into double-chain tPA completely under widely-varying conditions such as the kind of cells, the manner of cell cultivation and the cycle of cultivation. Namely, the kind and concentration of a proteolytic enzyme contained in a culture medium for cells generally differ from one medium to another and considerable difficulties are involved in controlling the action of such proteolytic enzymes. On the other hand, there is a wide variety of proteolytic enzyme inhibitors, including those giving adverse influence to the multiplication of cells. A limitation is therefore imposed on the kind of proteolytic enzyme inhibitors which are usable in the cultivation of cells. Furthermore, some kinds of proteolytic enzyme inhibitors are expensive and are hence impractical for use in cultivation on a large scale.

As a method for obtaining single-chain tPA in a pure form, it has also been known to use an immobilized monoclonal antibody which adsorbs single-chain tPA specifically (catalogue of Biopool AB, Sweden). This method is however accompanied by problems in the adsorbability to the immobilized monoclonal antibody and the stability of a column of the antibody during its use.

DISCLOSURE OF THE INVENTION

Under the foregoing circumstances, the present inventors have carried out an extensive investigation with a view toward developing a process for separating and purifying single-chain tPA from an aqueous medium in which both single-chain tPA and double-chain tPA are contained. As a result, it has been found that single-chain tPA and double-chain tPA are different in affinity to ETI and can be effectively separated from each other by changing the pH of an eluent, leading to completion of this invention.

Namely, the present invention provides a process for separating with ETI single-chain tPA and double-chain tPA from an aqueous medium containing both single-chain tPA and double-chain tPA, which comprises bringing the aqueous medium, which contains both single-chain tPA and double-chain tPA, into contact with an ETI-bearing carrier to adsorb the tPAs on the carrier, washing off proteinaceous impurities, eluting the single-chain tPA specifically in a pH range in which the single-chain tPA can be eluted, and then eluting the single-chain tPA and double-chain tPA or the double-chain tPA in a pH range in which the single-chain tPA and double-chain tPA can be eluted.

The process of this invention is applicable irrespective of the kind of tPA-producing cells. Namely, the present invention has made it possible to separate and purify single-chain tPA and double-chain tPA from any one of tPAs produced respectively by using melanoma cells, normal human cells, cells with the human tPA gene integrated therein in accordance with recombinant DNA technology, etc. Moreover, it is possible to separate, in pure forms, single-chain tPA and double-chain tPA from each other irrespective of the composition of a culture medium, in other words, from a serum-added medium in the same manner as in the case of a serum-free medium.

It is an absolutely new process that single-chain tPA and double-chain tPA are separated and isolated from each other by using such a column.

BEST MODE FOR CARRYING OUT THE INVENTION

The aqueous medium, which contains both single-chain tPA and double-chain tPA and is used in the process of this invention, is not limited by the kind of tPA-producing cells, in other words, is an aqueous medium containing single-chain tPA and double-chain tPA produced by using various kinds of cells, for example, melanoma cells, normal human cells, cells with the human tPA gene integrated therein in accordance with recombinant DNA technology, etc.

As a solution containing these tPA, it is also possible to use a solution obtained by partially purifying a culture broth of the above-described cells, which contains tPA produced, or a solution which is prepared in each step required for the separation and purification of single-chain tPA and double-chain tPA and contains both single-chain tPA and double-chain tPA.

As the above-described cells with the tPA gene integrated therein, namely, as cells transformed by a replicative expression vector, which can express the DNA sequence coding the active human tPA, out of host cells which have been transformed, may be mentioned Chinese hamster ovary cells, mouse fibroblast cells, mouse myeloma cells, human fetal amnion cells, HeLa cells, yeast cells and the like by way of example.

The ETI-bearing carrier, which is used in the process of this invention, is a carrier bearing in a form immobilized thereon an immobilizable Kunitz inhibitor which occurs in seeds of *Erythrina latissima* (plant of the legume family, broadleaf Erythrina) and other plants of the Erythrina species, and is an inhibitor for trypsin, plasmin and tPA but is in a form such that it does not act on urokinase.

As a carrier of the type that can immobilize ETI, it is possible to use insoluble agarose, dextran, cellulose, polyacrylamide, polyethylene glycol glycidyl methacrylate polymer or glass beads, or a combination of two or more of these carriers.

As a method for immobilizing ETI on a carrier, the following methods may be followed. For example, (a) immobilization using agarose activated with cyanogen bromide, (b) coupling employing a water-soluble carbodiimide, (c) glutaraldehyde coupling including binding of $NH_2$ groups of agarose which has been converted into the aminoalkyl form in advance, (d) coupling to agarose activated with an N-hydroxy-succinimide ester, (e) coupling by an epoxy-activated agarose, (f) (coupling by) periodic acid activated agarose obtained by forming aldehyde functional groups, reacting with the amine of ETI to form a Schiff base, and then reducing with sodium borohydride, (g) coupling using a bromoacetyl alkylamine agarose, (h) coupling using a diazonium derivative, etc. Regarding the carrier, (i) cellulose may be used in accordance with the method proposed by Parikh, et al. [W. B. Jakobi and M. Wilcheck: "Methods in enzymology", 34, 77–102, Academic Press, N.Y.] subsequent to its conversion into a hydrazide derivative, (j) polyacrylamide may be used by coupling it directly in accordance with the glutaraldehyde method or through the diazotization of a p-aminobenzamide derivative or hydrazide derivative, and (k) glass beads may be used in accordance with the method proposed by H. H. Weetall and A. M. Filbert, et al. (W. B. Jakobi and M. Wilcheck: "Methods in enzymology", 34, 59–72, Academic Press, N.Y.).

In the process of this invention, the above-described aqueous medium containing both single-chain tPA and double-chain tPA is brought into contact with such an ETI-bearing carrier as mentioned above.

No particular limitation is imposed on the operation for contacting the aqueous medium and carrier to each other. A usual method may be applied, for example, an operation in which they are contacted by the batch or column method.

In the case of the column method, the flow of the solution may be either an ascending stream or a descending stream. As the column, a cylindrical column is used dominantly in general. The diameter/height ratio of the column may be determined without any particular limitations.

The operating temperature should be within a temperature range where tPA remains stable, preferably, within a range of from the temperature, at which the aqueous medium does not freeze, to room temperature.

By the above operation for contacting the aqueous medium and carrier, the single-chain tPA and double-chain tPA both contained in the aqueous medium are adsorbed on the ETI-bearing carrier.

After the above adsorbing operation, the column may be washed as needed under conditions not eluting tPA, for example, by using a solution which contains a salt at a high concentration and has a pH in a range of from neutral to mild basicity, whereby various proteinacious impurities acted non-specifically on the carrier are removed.

According to the process of this invention, the ETI carrier with both single-chain tPA and double-chain tPA adsorbed thereon is then treated, firstly, with an eluent of such a pH range that single-chain tPA is eluted specifically, thereby eluting single-chain tPA from the ETI carrier to collect single-chain tPA, and then treating the ETI carrier, which bears the double-chain tPA adsorbed thereon and may also contain any remaining single-chain tPA, with an eluent of such a pH range that both single-chain tPA and double-chain tPA are eluted, thereby to elute tPA containing both single-chain tPA and double-chain tPA or double-chain tPA.

The pH range for eluting single-chain tPA specifically and the subsequent pH range for eluting both single-chain tPA and double-chain tPA vary depending on various factors involved in the respective eluents. It is however possible to elute single-chain tPA and double-chain tPA separately and to collect the intended single-chain tPA by choosing and applying suitable conditions with respect to the combination of such various factors.

The following may be mentioned by way of example as factors which are involved in the respective eluents and affect the above-mentioned pH ranges: (1) kind of buffer glycine-hydrochloric acid buffer, citrate buffer, tartrate buffer, phosphate buffer, acetate buffer, lactate buffer, succinate buffer, phthalate buffer, veronal buffer, etc.; (2) kind of salt: salts containing kaotropic ions, such as thiocyanates and perchlorates, sodium chloride, potassium chloride, calcium chloride, magnesium chloride, ammonium sulfate, etc.; (3) concentrations of buffer and salt; (4) additives: (A) basic amino acids such as arginine, and lysine and substances similar to basic amino acids, such as ornithine and e-aminocaproic acid, (B) competitive inhibitors for trypsin-like enzymes, such as benzamidine, (C) nucleophilic reagents such as amines and alcohols, (D) protein modifiers such as urea and guanidine hydrochloride, (E) surfactants such as Tween 80 and Triton X-100; etc.

These factors may be used either singly or as a mixture of two or more factors.

No particular limitation is imposed on the pH range in which the single-chain tPA is eluted specifically from the ETI carrier with both single-chain tPA and double-chain tPA adsorbed thereon. Since the eluting effects change in accordance with the buffer and the kinds and concentrations of salts used in an eluent and the kinds and concentrations of additives added as needed and also vary the type of a carrier for bearing ETI thereon and the bearing method, the optimal pH range also vary. The lower limit for the pH range for eluting single-chain tPA specifically ranges approximately from about 4 to about 5 or so in general. For specific elution of single-chain tPA, it is necessary to use an eluent having a pH within a range of the lower limit and higher. Further, no limitation is imposed either on the pH range in which single-chain tPA and double-chain tPA are eluted further from the ETI carrier subsequent to the elution of single-chain tPA. Since it is generally necessary to elute single-chain tPA and double-chain tPA which are still adsorbed on the ETI carrier after the specific elution of single-chain tPA, the PH range should be sufficient to elute not only single-chain tPA but also double-chain tPA. Both single-chain tPA and double-chain tPA can generally be eluted provided that the pH range is about 4–5 and lower.

When arginine, benzamidine, urea, guanidine hydrochloride or the like is added out of the various additives described above, the effects for the separation of single-chain tPA and double-chain tPA from each other can be increased further. When such an additive is incorporated, the pH range in which single-chain tPA is specifically eluted varies further due to its incorporation. Although not limiting, the optimum pH range is usually from about pH 4.5 to pH 6 and single-chain tPA and double-chain tPA can be eluted by an eluent whose pH is lower than pH 4.5.

The concentration of arginine, benzamidine, urea, guanidine hydrochloride or the like employed for the elution of single-chain tPA may range from 1 mM to the upper limit concentration for its dissolution. Within the range of from pH 4.5 to pH 6.0 for example, benzamidine can be used at a lower concentration as the pH approaches 4.5 while a higher benzamidine concentration is needed as the pH becomes closer to 6.

Although arginine, benzamidine, urea or guanidine hydrochloride used herein has been known to bind competitively to the center of activity of serine protease to dissociate the complex, it is an absolutely-unknown novel effect that such an additive shows effectiveness for the separation of single-chain tPA and double-chain tPA.

An eluent of a selected pH range is prepared by using a buffer, salt and the like of kinds, which are selected respectively from the above-described buffers, salts and the like in accordance with the purpose, at concentrations chosen depending on the purpose and if necessary, incorporating one or more additives.

In the process of this invention, the batch method, column method or the like can be used in the operation in which single-chain tPA and double-chain tPA adsorbed on an ETI carrier are eluted respectively.

In the case of the batch method, an eluent whose pH is controlled within a range set for selective elution of single-chain tPA and an ETI carrier with single-chain tPA and double-chain tPA adsorbed therein are stirred and mixed and are then left over. By this operation, the single-chain tPA is eluted from the ETI carrier and moves into a supernatant. The supernatant is recovered so that the single-chain tPA can be obtained at a high purity. If there is any single-chain tPA still remaining without elution, the ETI carrier with the single-chain tPA and double-chain tPA adsorbed thereon is stirred and mixed with another eluent whose pH has been adjusted so as to elute both single-chain tPA and double-chain tPA, and the resulting mixture is then left over. By this operation, the double-chain tPA which may contain single-chain tPA is eluted from the ETI carrier and moves into a supernatant. By collecting this supernatant, it is possible to obtain double-chain tPA which may contain single-chain tPA. tPA which contains single-chain tPA and is composed principally of double-chain tPA may be subjected to further separation into single-chain tPA and double-chain tPA by s suitable method as needed.

In the case of the column method, an eluent prepared similarly within a pH range set for specific elution of single-chain tPA is caused to flow through a column packed with an ETI carrier with single-chain tPA and double-chain tPA adsorbed thereon, whereby the single-chain tPA is eluted from the ETI carrier and single-chain tPA can hence be obtained at a high purity in a form dissolved in the eluent. Subsequently, another eluent of a pH range in which both single-chain tPA and double-chain tPA can be eluted is caused to flow. As a result, single-chain tPA, which may still remain adsorbed on the ETI carrier, and double-chain tPA are eluted, so that double-chain tPA which may contain single-chain tPA can be obtained in a form dissolved in the latter eluent. The tPA composed principally of double-chain tPA and also contains single-chain tPA may be separated further into single-chain tPA and double-chain tPA by a suitable method as needed.

In these methods, the flow of each of the eluents through the column may be either an ascending stream or a descending stream and tPA can be eluted without being affected by the flow velocity. Faster flow velocities are however not preferable, because the elution of tPA tends to occur as broader fractions as the flow velocity increases.

The elution of tPA is practised within a temperature range where tPA remains stable, preferably, within a range of from the temperature, at which the aqueous medium does not freeze, to room temperature.

BEST MODE FOR CARRYING OUT THE INVENTION.

The process of this invention will hereinafter be described specifically by Examples.

EXAMPLE 1

Preparation of affinity reagent (ETI reagent):

An ETI reagent useful in the practice of this invention was prepared for its use in a Sepharose column in the following manner. Seeds of Erythrina latissima were collected and processed in accordance with the method proposed by Joubert, et al. [F. J. Joubert, et al.: "Hoppe-Seyler's Z. Physiol. Chem.", 362, 531–538 (1981)]. The seeds were ground, defatted, and then extracted overnight at 10° C. in a 0.5 M/l saline.

The extract was centrifuged, the precipitate was discarded, and the supernatant thus obtained was subjected to precipitation with ammonium sulfate, followed by collection of the resultant precipitate. The precipitate was thereafter subjected to chromatography on Sephadex G-50, DEAE-cellulose and DEAE-cellulose.

When the purified product thus obtained was subjected to electrophoresis in a 15% polyacrylamide gel containing 0.1% of sodium dodecylsulfate (SDS), the product migrated as a single band of an apparent molecular weight of 22,000 daltons.

The above purified product was caused to bind to cyanogen bromide activated agarose by a usual method. Using the resultant product, single-chain tPA and double-chain tPA were purified in the following manner.

After stabilizing, with Tween 80 (0.02%) and saline (1 M/l), 2 l of a culture supernatant prepared from a culture of Bowes melanoma cells (ATCC CRL 1424 G361) whose culture medium contained 10% of thermo-inactivated (56° C., 30 minutes) fetal calf serum and 20 KIU/ml of aprotinin, it was charged into a column of ETI-Sepharose (25 mg ETI/5 ml resin).

The column effluent was collected and the plasminogen-dependent fibrinolytic activity was measured. About 10% of the activity charged into the column was observed.

This eluted fraction was analyzed by zymography after subjecting same to electrophoresis in a polyacrylamide gel. As plasminogen activators, two bands were observed at 110,000±20,000 daltons and about 70,000 daltons respectively.

Thereafter, the ETI-Sepharose column was washed with 20 column volumes of a 2M saline which contained 0.2% of Tween 80. By this method, about 5% of the activity applied to the column was detected. Bands of 110,000±20,000 and about 70,000 daltons were observed as plasminogen activators on a zymograph.

The thus-adsorbed proteins were eluted in accordance with a linear gradient technique ranging from pH 6.5 to pH 3.0, using a 0.2M veronal buffer containing 0.2M of benzamidine and 0.15M of sodium chloride.

By the above method, a peak was obtained in a range of from pH 6.0 to pH 4.5 and another peak in a range of from pH 4.5 to pH 3.5. A combination of these two fractions indicated 80–85% of the activity applied to the column.

A sample which had been reduced with mercaptoethanol was investigated by the silver staining subsequent to its electrophoresis in a polyacrylamide gel. As a result, the substance eluted in the range of from pH 6.0 to pH 4.5 was not changed in molecular weight even when reduced and indicated about 70,000 daltons, but when the substance eluted in the range of from pH 4.5 to pH 3.5 was reduced, the band of about 70,000 daltons disappeared mostly and a new band appeared around 30,000±40,000 daltons.

From the above result, it has been found that the tPA eluted in the range of from pH 6 to pH 4.5 was single-chain tPA and the tPA eluted in the range of from pH 4.5 to pH 3.5 was substantially double-chain tPA. Incidentally, the treatment of the column was carried out at room temperature.

EXAMPLE 2

After culturing Bowes melanoma cells (ATCC CRL 1424 G361) in RPMI-1640 culture medium supplemented with 10% of thermoinaactivated (56° C., 30 minutes) fetal calf serum, the cells were washed once and then cultured for 24 hours in a serum-free medium. The medium was then collected as a culture crop. To 50 l of the culture crop, sodium chloride was added to a final concentration of 1M.

The resulting solution was washed with a 0.05M phosphate buffer (pH 7.5) containing 1.0M of sodium chloride in a column. The column effluent and washing were combined and the plasminogen-dependent fibrinolytic activity was measured. About 10% of the whole activity charged into the column was detected. After electrophoresis in an SDS polyacrylamide gel, a band of 110,000±20,000 daltons was observed on a zymograph. The protein adsorbed on the column was eluted with a 0.05M $NaH_2PO_4$—NaOH solution (pH 5.0) containing 0.5M of ammonium thiocyanate. By the above method, about 50% of the activity charged into the column was recovered. By the silver staining subsequent to electrophoresis in an SDS polyacrylamide gel, a single band corresponding to a molecular weight of 70,000 daltons was observed. No low molecular weight band was detected even after reduction with mercaptoethanol.

From the above results, it was confirmed that double-chain tPA was not contained in the above fraction. On the other hand, the remaining adsorbed protein was eluted at pH 3.5 with a 0.1M glycine-hydrochloric acid buffer which contained 0.5M of sodium chloride. By this method, about 40% of the activity applied to the column was found in the eluate. By the silver staining subsequent to electrophoresis in an SDS polyacrylamide gel, bands corresponding respectively to molecular weights of 70,000 daltons and about 30,000 daltons were observed. In the case of a sample obtained subsequent to reduction with mercaptoethanol, the band of about 70,000 daltons disappeared practically and a band was found newly in a molecular weight range of from about 30,000–40,000 daltons. From the above results, the fraction was found substantially to be double-chain tPA. Incidentally, the treatment of the column was carried out at room temperature.

EXAMPLE 3

After stabilizing, with Tween 80 (0.02%) and saline (1 M/l), 2 l of a culture supernatant prepared from a culture of fetal human foreskin cells ("Flow 7000", product of Dainippon Pharmaceutical Co., Ltd.) whose culture medium contained 10% of thermoinactivated (56° C., 30 minutes) fetal calf serum and 20 KIU/ml of aprotinin, it was charged into a column of ETI-Sepharose (25 mg ETI/5 ml resin) prepared by immobilizing ETI on cyanogen bromide activated agarose.

The column effluent was collected and the plasminogen-dependent fibrinolytic activity was measured. About 45% of the activity charged into the column was observed.

This eluted fraction was analyzed by zymography after subjecting same to electrophoresis in a polyacrylamide gel. As plasminogen activators, were observed 2-3 bands around 100,000 daltons, 2-3 bands around 50,000-70,000 daltons, and one band around 35,000 daltons. daltons.

The ETI-sepharose column with tPA adsorbed therein was washed with 20 column volumes of a 0.1M NaH buffer (pH 9.5) containing 2.0M of sodium chloride.

By this method, about 5% of the activity applied to the column was detected. Bands identical to those obtained above were observed on a zymograph.

As buffers for elution, were used a 0.1M phosphate buffer (pH 5.5) containing 0.3M of lysine and 0.15M sodium chloride and a 0.2M citrate buffer (pH 3.0) containing 0.15M of sodium chloride.

A combination of the thus-eluted two fractions of different pHs indicated 40–45% of the activity applied to the column.

A sample which had been reduced with mercaptoethanol was investigated by the silver staining subsequent to its electrophoresis in a polyacrylamide gel. The substance eluted at pH 5.5 was not changed in molecular weight even when reduced and indicated about 70,000 daltons, but when the substance eluted at pH 3.0 was reduced, the band of about 70,000 daltons disappeared mostly and a new band appeared around 30,000–40,000 daltons.

From the above result, it was fount that the tPA eluted at pH 5.5 was single-chain tPA and the tPA eluted at pH 3.0 was double-chain tPA. Incidentally, the treatment of the column was carried out at room temperature.

EXAMPLE 4.

After stabilizing, with 1M saline, 2 l of a culture supernatant prepared from a culture of mouse fibroblast cells with the human tPA gene (Japanese Patent Laid-Open No. 264918/1985) integrated therein (Mouse C1271 ATCC CRL 1616) whose culture medium contained 2% of thermoinactivated (56° C., 30 minutes) fetal calf serum and 20 KIU/ml of aprotinin, it was charged into a column of ETI-Sepharose (25 mg ETI/5 ml resin) prepared by immobilizing ETI on cyanogen bromide activated agarose.

The column effluent was collected and the plasminogen-dependent fibrinolytic activity was measured. About 10% of the activity applied to the column was observed.

This eluted fraction was analyzed by zymography after subjecting same to electrophoresis in an SDS polyacrylamide gel. As plasminogen activators, two types of substances were observed respectively at 110,000±20,000 daltons and about 70,000 daltons.

After causing the whole solution to flow though an ETI-Sepharose column, the column was washed with 20 column volumes of a 2.0M of saline. By this method, about 5% of the activity applied to the column was detected. Bands of 110,000±20,000 daltons and about 70,000 daltons were observed as plasminogen activators on a zymograph.

The proteins adsorbed on the ETI-Sepharose column were eluted by using a 0.1M citrate buffer (pH 4.7) containing 0.15M of sodium chloride and a 0.1M citrate buffer (pH 3.0) containing 0.15M of sodium chloride. A combination of these two fractions indicated about 80% of the activity applied to the column.

A sample which had been reduced with mercaptoethanol was investigated by the silver staining subsequent to its electrophoresis in a polyacrylamide gel. The substance eluted at pH 4.7 was not changed in molecular weight even when reduced and indicated about 70,000 daltons, but when the substance eluted at pH 3.0 was reduced, the band of about 70,000 daltons disappeared mostly and a new band appeared around 30,000–40,000 daltons.

From the above results, it was found that the tPA eluted at pH 4.7 was single-chain tPA and the tPA eluted at pH 3.0 was mostly double-chain tPA. Incidentally, upon treatment of the column, the adsorbed tPA was eluted by causing the eluents to flow in the opposite direction and the elution was conducted at 4° C.

EXAMPLE 5

After stabilizing, with 1M saline, 10 l of a culture supernatant prepared from a culture of mouse fibroblast cells with the human tPA gene (Japanese Patent Laid-Open No. 264918/1985) integrated therein (Mouse C1271 ATCC CRL 1616) whose culture medium contained 2% of thermoinactivated (56° C., 30 minutes) fetal calf serum and 20 KIU/ml of aprotinin, a column of ETI-Sepharose (25 mg ETI/5 ml resin) prepared by immobilizing ETI on AH-agarose (Pharmacia AB) was added. After stirring the resultant mixture at 4° C. for 30 minutes, it was filtered through a glass filter so that the resin was collected. Thereafter, the resin was washed with 20 bed volumes of a 20M saline. The resin with tPA adsorbed thereon was eluted first with a 0.1M sodium phosphate buffer (pH 6.0) containing 2M of urea and then with a 0.1M citrate buffer (pH 3.0) containing 0.15M of sodium chloride, whereby tPA was eluted. A combination of these two fractions indicated about 80% of the activity applied to the column.

A sample which had been reduced with mercaptoethanol was investigated by the silver staining subsequent to its electrophoresis in a polyacrylamide gel. The substance eluted at pH 6.0 was not changed in molecular weight even when reduced and indicated about 70,000 daltons, but when the substance eluted at pH 3.0 was reduced, the band of about 70,000 daltons disappeared mostly and a new band appeared around 30,000–40,000 daltons.

From the above results, it was found that the tPA eluted at pH 6.0 was single-chain tPA and the tPA eluted at pH 3.0 was mostly double-chain tPA.

EXAMPLE 6

Sodium chloride was added to a final concentration of 1M to 2 l of a culture supernatant prepared from a culture of Chinese hamster ovary (CHO) cells with the human tPA gene integrated therein (ATCC CRL 61 cells) whose culture medium contained 10% of thermoinactivated (56° C., 30 minutes) fetal calf serum and 40 KIU/ml of aprotinin. After causing the solution to pass through ETI-Sepharose (25 mg ETI/5 ml resin) which had been equilibrated with a 0.05M phosphate buffer (pH 7.5) containing 1.0M of sodium chloride, the column was washed with a 0.05M $Na_2HPO_4$—NaOH buffer (pH 9.5) containing 2.0M of sodium chloride and 10 mM of arginine.

In the manner described above, about 10% of the activity charged into the column flowed out and bands corresponding respectively to molecular weights of 110,000±20,000 and about 70,000 daltons were observed on a zymogram.

The proteins adsorbed were eluted with a 0.05M $NaH_2PO_4$—NaOH solution (pH 4.4) which contained 0.01M of arginine and 0.1M of sodium chloride.

The activity of the eluate was found to be about 65% of the activity charged into the column.

The remaining adsorbed protein was dissolved with a 0.1M citrate buffer (pH 3.0) containing 0.1M of sodium chloride About 25% of the activity charged into the column was observed.

A sample which had been reduced with mercaptoethanol was investigated by the silver staining subsequent to its electrophoresis in a polyacrylamide gel. The substance eluted at pH 4.4 was not changed in molecular weight even when reduced and indicated about 70,000 daltons, but when the substance eluted at pH 3.0 was reduced, the band of about 70,000 daltons disappeared mostly and a new band appeared around 30,000–40,000 daltons.

From the above results, it was found that the tPA eluted at pH 4.4 was single-chain tPA and the tPA eluted at pH 3.0 was mostly double-chain tPA.

EXAMPLE 7

Sodium chloride was added to a final concentration of 1M to 50 l of a culture supernatant prepared from a culture of Chinese hamster ovary (CHO) cells with the human tPA gene integrated therein (ATCC CCL 61) whose culture medium contained 10% of thermo-inactivated (56° C., 30 minutes) fetal calf serum and 40 KI-U/ml of aprotinin. The solution was added to an ETI-Sepharose (25 mg ETI/5 ml resin) column which had been equilibrated with a 0.05M phosphate buffer (pH 7.5) containing 1.0M of sodium chloride. After stirring at 4° C. for 30 minutes, the mixture was filtered through a glass filter to collect the resin. The resin was thereafter washed with a 0.05M $Na_2HPO_4$ solution (pH 9.5). After packing the resin with tPA adsorbed thereon in a column, proteins adsorbed were eluted with a 0.05M lactate buffer (pH 4.8) which contained 0.1M of sodium chloride and 2% ethanol.

The activity of the eluate was found to be about 60% out of total activity charged to the resin.

The remaining adsorbed proteins were eluted with a 0.1M lactate buffer (pH 3.0) containing 0.1M of sodium chloride. About 25% out of total activity charged to the resin was indicated.

A sample which had been reduced with mercaptoethanol was investigated by the silver staining subsequent to its electrophoresis in a polyacrylamide gel. The substance eluted at pH 4.8 was not changed in molecular weight even when reduced and indicated about 70,000 daltons, but when the substance eluted at pH 3.0 was reduced, the band of about 70,000 daltons disappeared mostly and a new band appeared around 30,000±40,000 daltons.

From the above results, it was found that the tPA eluted at pH 4.5 was single-chain tPA and the tPA eluted at pH 3.0 was mostly double-chain tPA.

EXAMPLE 8

Sodium chloride was added to a final concentration of 1M to 2 l of a culture supernatant prepared from a culture of fetal amnion cells with the human tPA gene integrated therein (FL, ATCC CCL-62) by using human cytomegalovirus (HCMV) as a human tPA expression promoter, whose culture medium contained 2% of thermo-inactivated (56° C., 30 minutes) fetal calf serum and 20 KIU/ml of aprotinin. The solution was thereafter charged into a column of ETI-Sepharose (25 mg ETI/5 ml resin) obtained by immobilizing ETI on cyanogen bromide activated agarose.

A column effluent was collected and its plasminogen-dependent fibrinolytic activity was measured. About 10% of the activity applied to the column was observed.

This effluent fraction was analyzed by zymography after its electrophoresis in an SDS polyacrylamide gel. As plasminogen activators, two kinds of substances of 110,000±20,000 daltons and about 70,000 daltons were observed.

After causing the entire solution to pass through the ETI-Sepharose column, the column was washed with 20 column volumes of a 2.0M saline. By this method, about 5% of the activity charged into the column was detected. On a zymograph, bands of 110,000±20,000 daltons and about 70,000 daltons were found as plasminogen activators.

Proteins adsorbed on the ETI-Sepharose column were eluted by using a 0.1M citrate buffer (pH 4.7) containing 0.3M arginine and 0.15M of sodium chloride and a 0.1M citrate buffer (pH 3.0) containing 0.15M of sodium chloride. A combination of these two effluent fractions indicated about 80% of the activity charged.

A sample which had been reduced with mercaptoethanol was investigated by the silver staining subsequent to its electrophoresis in a polyacrylamide gel. The substance eluted at pH 5.5 was not changed in molecular weight even when reduced and indicated about 70,000 daltons, but when the substance eluted at pH 3.0 was reduced, the band of about 70,000 daltons disappeared mostly and a new band appeared around 30,000±40,000 daltons.

From the above results, it was found that the tPA eluted at pH 5.5 was single-chain tPA and the tPA eluted at pH 3.0 was mostly double-chain tPA.

EXAMPLE 9

A host enzyme (*Saccharomyces cerevisiae*) transformed with the human tPA gene integrated therein was allowed to grow by a known method, namely, by the method described in "Principles and Practice of Recombinant DNA Research with Yeast in The Molecular Biology of Yeast Saccharomyces: Metabolism and Gene Expression", pp 603–636, Cold Spring Harbor Laboratory, Cold Spring Harbor, N.Y. (1982).

The resultant cells were ground with glass beads. tPA was extracted with a 0.05M phosphate buffer (pH 7.5) which contained 1M sodium chloride and 0.02% of Tween 80. The extract was filtered to obtain a filtrate.

The filtrate (1 l) was caused to flow through a column of ETI-Sepharose (25 mg ETI/5 ml resin). Thereafter, the column was washed with 20 column volumes of a 2.0M saline containing 0.02% of Tween 80. The tPA adsorbed was eluted firstly with a 0.1M citrate buffer (pH 3.0) containing 0.02% of Tween 80 and 0.5M of ammonium sulfate.

A sample which had been reduced with mercaptoethanol was investigated by the silver staining subsequent to its electrophoresis in a polyacrylamide gel. The substance eluted at pH 5.0 was not changed in molecular weight even when reduced and indicated about 70,000 daltons, but when the substance eluted at pH 3.0 was reduced, the band of about 70,000 daltons disappeared mostly and a new band appeared around 30,000±40,000 daltons. From the above results, it was found that the tPA eluted at pH 5.0 was single-chain tPA and the tPA eluted at pH 3.0 was mostly double-chain tPA.

We claim:

1. A process for separating single-chain tPA and double-chain tPA from each other, which comprises bringing an aqueous medium, which contains both single-chain tPA and double-chain tPA, into contact with an Erythrina trypsin inhibitor-bearing carrier to adsorb the tPAs on the carrier eluting the single-chain tPA specifically in a pH range of 4.4 to 6.0, and then eluting a mixture of the tPAs that is mainly double-chain tPA in a pH lower than 4.4.

* * * * *